United States Patent [19]

Engel

[11] 4,160,842*

[45] Jul. 10, 1979

[54] INSECTICIDAL [β-(SUBSTITUTED-PHENYL)VINYL]CYCLOPROPANECARBOXYLATES

[75] Inventor: John F. Engel, Medina, N.Y.

[73] Assignee: FMC Corporation, Philadelphia, Pa.

[*] Notice: The term of this Patent subsequent to Jun. 5, 1996 has been disclaimed.

[21] Appl. No.: 718,253

[22] Filed: Aug. 27, 1976

[51] Int. Cl.$^2$ .................. C07C 69/76; C07C 121/64; A01N 9/24
[52] U.S. Cl. .................. 424/274; 260/465 D; 542/426; 542/429; 560/8; 560/18; 560/21; 560/48; 560/64; 560/73; 560/101; 560/102; 562/405; 562/432; 562/435; 562/456; 562/474; 562/491; 562/492; 424/282; 424/285; 424/304; 424/308; 424/309
[58] Field of Search ............. 260/465 D, 469, 468 H, 260/240 R; 560/8, 18, 21, 48, 73, 101, 102; 542/426, 429; 424/274, 282, 285, 304, 308, 309

[56] References Cited

U.S. PATENT DOCUMENTS

| | | | |
|---|---|---|---|
| 3,723,469 | 3/1973 | Martel | 260/468 |
| 3,786,052 | 1/1974 | Martel et al. | 260/240 R |
| 4,024,163 | 5/1977 | Elliott et al. | 560/8 |

FOREIGN PATENT DOCUMENTS 1580474  9/1969  France ..................... 260/468

OTHER PUBLICATIONS

Ito et al., J. Org. Chem., vol. 39, No. 12, pp. 1763–1765 (1974).

*Primary Examiner*—Jane S. Myers
*Attorney, Agent, or Firm*—Robert M. Kennedy; H. Robinson Ertelt

[57] ABSTRACT

New insecticidal (β-phenylvinyl)cyclopropanecarboxylates having on the phenyl ring one or more substituents such as halogen, cyano, nitro, lower alkyl, aryl, aralkyl, lower alkoxy, lower alkylthio, aryloxy, arylthio, lower haloalkyl, di(lower alkyl)amino, or methylenedioxy are described, and their preparation and insecticidal utility are exemplified.

10 Claims, No Drawings

INSECTICIDAL [β-(SUBSTITUTED-PHENYL)VINYL]CYCLOPROPANECARBOXYLATES

This invention relates to the general field of insecticides, particularly to insecticides for use in agriculture to protect crops and animals, but also for household and insecticidal use. The active compounds of this invention are insecticidal esters of 2,2-dimethyl-3-[β-(substituted-phenyl)vinyl]cyclopropanecarboxylic acid.

Ever since the structures of naturally occurring pyrethroids were elucidated, synthesis efforts have been directed toward the preparation of related compounds of enhanced insecticidal activity and improved stability toward air and light. A noteworthy advance in this area was the discovery by Elliott et al of certain highly active compounds remarkably resistant to photooxidative degradation, for example, 3-phenoxybenzyl 3-(β,β-dichlorovinyl)-2,2-dimethylcyclopropanecarboxylate, Nature, 246, 169 (1973), Belgian Pat. Nos. 800,006 and 818,811.

Despite the extensive activity in the field of insecticidal cyclopropanecarboxylates, insecticidal, 2,2-dimethyl-3-[β-(substituted-phenyl)vinyl]cyclopropanecarboxylates have not been described prior to the present invention.

The compounds of the present invention have the formula:

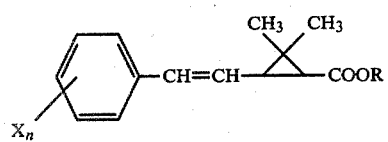

in which X is halogen, such as fluoro, chloro, or bromo, cyano, nitro,, aryl,, such as phenyl, thienyl, furyl, or pyridyl, aralkyl, such as benzyl,, lower alkyl, lower haloalkyl, lower alkoxy, lower alkylthio, aryloxy, arylthio, di-(lower alkyl)amino, and methylenedioxy; n is 1, 2, or 3, more commonly 1 or 2; and R is the residue of an alcohol which in combination with an appropriate acid moiety yields an insecticidal cyclopropanecaboxylate. A wide range of such alcohols are known to the insecticide art. Those R groups useful in compounds of the present invention include:

(1) a benzyl- or phenoxy-substituted benzyl group of the formula:

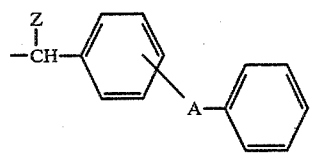

wherein Z is hydrogen, methyl, cyano, ethynyl, or phenyl, and A is —O— or —CH₂—;

(2) a benzyl- or phenoxy-substituted furylmethyl group such as 5-benzyl-3-furylmethyl;

(3) an imidomethyl group such as maleimidomethyl, phthalimidomethyl, and tetrahydrophthalimidomethyl;

(4) a benzyl group substituted in at least two ring positions with chloro, methyl, or methylenedioxy groups, for example 3,4-methylenedioxybenzyl, 2-chloro-4,5-methylenedioxybenzyl, and 2,4-dimethylbenzyl;

(5) a substituted cyclopentenonyl group such as allethrolonyl.

The more readily available R groups which give active insecticides of the present invention are 3-phenoxybenzyl, α-cyano-3-phenoxybenzyl, and 5-benzyl-3-furylmethyl.

In the substituent X, lower means having one to four carbon atoms, preferably, and particularly for the haloalkyl and amino substituents, having one or two carbon atoms. Examples of halomethyl substituents include trichloromethyl and trifluoromethyl groups.

The preparation and insecticidal properties of the compounds of this invention are illustrated in the following specific examples. Unless otherwise specified, all temperatures are in degrees centigrade, and concentration of liquid volume was carried out under the reduced pressure produced by a water aspirator.

EXAMPLE 1

Synthesis of α-Cyano-3-phenoxybenzyl 3-[β-(4-chlorophenyl)-vinyl]2,2-dimethylcyclopropanecarboxylate

A. Preparation of Ethyl 3-[β-(4-chlorophenyl)vinyl]-2,2-dimethylcyclopropanecarboxylate Under a nitrogen atmosphere and anhydrous conditions 81 ml of an approximately 2.5 M solution of n-butyllithium in hexane was added to a suspension of 84.54 g of 4-chlorobenzyltriphenylphosphonium chloride in 200 ml anhydrous benzene over a period of 20 min. The n-butyllithium solution was added in small portions, and the reaction temperature was maintained at about 25° by intermittent cooling with an ice-water bath. After addition of the n-butyllithium solution was completed, the reaction mixture was stirred at room temperature for 2.75 hours. This mixture was added, in 10–20 ml portions via a glass tube, to an anhydrous, ice cold, stirred solution of 32.20 g ethyl caronaldehyde in 50 ml of benzene. During the addition the reaction mixture was cooled with ice-water bath. The reaction mixture was allowed to warm to room temperature over a period of 0.5 hr and then stirred for an additional hour. The reaction mixture was filtered, and the filtrate was washed with two 200 ml portions of water, then with two 100 ml portions of saturated brine, and dried over anhydrous magnesium sulphate. The solvent was removed and the residue dried under reduced pressure to yield an amorphous white solid. The solid was triturated with 150 ml anhydrous hexane, filtered and concentrated to yield 44.88 g of viscous liquid. The nmr and ir spectra were consistent with the expected mixture of geometric isomers of ethyl 3-[β-(4-chlorophenyl)vinyl]-2,2-dimethylcyclopropanecarboxylate.

B. Preparation of 3-[β-(4-Chlorophenyl)vinyl]-2,2-dimethylcyclopropanecarboxylic acid A mixture of 37.90 g of ethyl 3-[β-(4-chlorophenyl)-vinyl]-2,2-dimethylcyclopropanecarboxylate, 6.56 g of sodium hydroxide, 371 ml of ethanol, and 21.5 ml of water was heated at 55° for 60 hours. After the mixture had stood at room temperature for 12 hours, the reaction mixture was concentrated under reduced pressure. The concentrate was diluted with 450 ml of dry benzene, then taken to dryness under reduced pressure. The residue was shaken with a mixture containing 400 ml of water and 100 ml saturated brine, then the resulting mixture was extracted with chloroform. The aqueous phase was made acidic (pH 3) with 320 ml of 3% hydrochloric acid, and extracted with a 500 ml portion of diethyl ether followed by two 1200 ml portions of diethyl ether. The ethereal extracts were washed with four 300 ml portions of water and then dried over anhydrous magnesium chloride. The dried ethereal solution was filtered and the solvent removed under reduced pressure to yield as an oil 33.06 g of 3-[β-(4-chlorophenyl)vinyl]-2,2-dimethylcyclopropanecarboxylic acid. The nmr and ir spectrum were consistent with the expected isomeric mixture.

C. Preparation of trans-3-[β-(E)-(4-Chlorophenyl)-vinyl]-2,2-dimethylcyclopropanecarboxylic acid A mixture (33.06 g) of geometric isomers, prepared as described above, was stirred for 15 min. at room temperature in 200 ml of pentane and filtered. The residue was collected and dried to yield 5.75 g of solid, mp 139.5°–140° identified by its nmr spectrum as trans-3-[β-(E)-(4-chlorophenyl)vinyl]-2,2-dimethylcyclopropanecarboxylic acid. An additional 2.79 g of this isomer was obtained by reducing the volumn of the filtrate by about ½ and cooling the concentrated filtrate to 0°. (The filtrate, containing other isomeric acids, was reserved). The nmr spectrum was definitive for the assigned structure.

D. Preparation of α-cyano-3-phenoxybenzyl trans-3-[β-(E)-(4-chlorophenyl)vinyl]-2,2-dimethylcyclopropanecarboxylate Trans-3-[β-(E)-(4-chlorophenyl)vinyl]-2,2-dimethylcyclopropanecarboxylic acid (8.34 g) was heated under reflux for 3 hours with 5 ml of thionyl chloride in 35 ml of benzene. The excess thionyl chloride and benzene were distilled from the reaction mixture. Additional benzene was added to the reaction mixture to bring the volume of the solution to 100 ml. A 24 ml portion of this solution containing 2.14 g of trans-3-[β-(E)-(4-chlorophenyl)vinyl]-2,2-dimethylcyclopropanecarbonyl chloride was treated with a mixture of 1.79 g of α-cyano-3-phenoxybenzyl alcohol, and 1.59 ml of pyridine in 10 ml of benzene. The addition of the alcohol mixture to the acid chloride was done at 0°. Upon complete addition the reaction mixture was stirred at ambient temperature for 24 hours; then was filtered to remove pyridine hydrochloride. The filtrate was evaporated under reduced pressure to a residual 3.50 g of oil. The oil was purified on a chromatographic column of 17.5 g of silica gel. Elution of the oil from the column was accomplished with diethyl ether/pentane mixtures. The yield was 2.60 g (71.0%) of α-cyano-3-phenoxybenzyl trans-3-[β-(E)-(4-chlorophenyl)-vinyl]-2,2-dimethylcyclopropanecarboxylate.

Analyses: Calc'd for $C_{28}H_{24}ClNO_3$: C 73.43; H 5.28; N 3.06. Found: C 73.18; H 5.32; N 2.98.

E. Preparation of α-cyano-3-phenoxybenzyl cis,trans-3-[β-(E,Z)-(4-chlorophenyl)vinyl]-2,2-dimethyl cyclopropanecarboxylate The final filtrate of Example I-C contained mixed isomeric acids depleted as to the trans (E) isomer. A portion of this acid, 5.60 g of cis,trans-3-[β-(E,Z)-(4-chlorophenyl)vinyl]-2,2-dimethylcyclopropanecarboxylic acid, was esterified by the method of Example I-D with 2.73 g of thionyl chloride, 5.18 g of α-cyano-3-phenoxybenzyl alcohol, and 3.5 ml of pyridine in benzene. The crude product was purified on a chromatographic column of 54.5 of silica gel. Elution was accomplished using 20% methylene chloride – 80% pentane to give 6.95 g (72%) of α-cyano-3-phenoxybenzyl cis,-trans-3-[β-(E,Z)-(4-chlorophenyl)vinyl]-2,2-dimethylcyclopropanecarboxylate.

Analyses: Calc'd for $C_{28}H_{24}ClNO_3$: C 73.43; H 5.28; N 3.06. Found: C 73.20; H 5.32; N 3.01.

EXAMPLE 2

Toxicity to Insects and Mites

Initial Contact Activity: One quarter gram of test compound was dissolved in 20 ml of acetone and this solution was dispersed in 180 ml of water containing one drop of isooctylpenyl polyethoxyethanol. Aliquots of this solution, which corresponds to 1250 ppm of active ingredient, were diluted with an appropriate amount of water to provide solutions containing 312 ppm or 156 ppm of active ingredient. Test organisms and techniques were as follows: the activity against the southern armyworm (*Spodoptera eridania* [Cram.]) was evaluated by dipping the leaves of pinto bean plants into the test solution and infesting the leaves with the appropriate immature-form insects when the foliage had dried; the activity against the pea aphid (*Acyrthosiphon pisum* [Harris]) was evaluated on broad bean plants whose leaves were dipped before infestation with adult aphids; the activity against two-spotted spider mites (*Tetranychus urticae* Koch) was evaluated on pinto bean plants whose leaves were dipped after infestation with adult mites; the activity against the milkweed bug (*Oncopeltus fasciatus* [Dallas]) was evaluated by spraying the test solutions into glass dishes or jars containing the adult insects. All organisms in the test were maintained in a holding room at 80° F. and 50% relative humidity for an exposure period of 48 hours. At the end of this time, the dead and living insects or mites were counted, and the percent kill was calculated. Results of these tests are summarized in Table 1.

EXAMPLE 3

Insecticidal Activity Against House Flies and German Cockroaches

In this test the compounds of this invention were tested for insecticidal activity against three or four day old female houseflies (resistant) (*Musca domestica* Linnaeus) and male German cockroaches [Blattella germanica [Linnaeus)]. A number of insects was anesthetized with carbon dioxide and placed in a container for about 2 hours, during which time the insects recovered to normal activity. The container confining the insects was fitted with a plunger which is used to force the insects against a nylon mesh at one end of the container. For the Level I test one microliter of an acetone solution containing five micrograms of the candidate insecticide, for the Level II test one microliter of an acetone solution containing one microgram of the candidate insecticide, was applied topicaly to each insect. The plunger was withdrawn and the insects were allowed to move freely about the container. Knockdown counts were recorded 10 minutes after treatment of houseflies and 30 minute after treatment of cockroaches. Percent mortality readings were made after 18–24 hours. Test results are set forth in Table 2. The ester of Example 1-E, prepared from the isomer mixture from which substantial removal of trans (E) isomer had been made, is clearly more insecticidally active than the ester of Example 1-D, prepared from the separated trans (E) isomer.

It is anticipated that, in the normal use of the compounds of the present invention as insecticides, the compounds will usually not be employed free from admixture or dilution, but will ordinarily be used in a suitable formulated state compatible with the method of application. The insecticidal cyclopropanecarboxylates of this invention may be formulated with the usual additives and extenders used in the preparation of pesticidal compositions. The toxicants of this invention, like most pesticidal agents, are incorporated with the adjuvants and carriers normally employed for facilitating the dispersion of active ingredients, recognizing the accepted fact that the formulation and mode of application of a toxicant may affect the activity of the material. The present compounds may be applied, for example, as a spray, dust, or granule, to the area in which pest control is desired, the choice of application varying of course with the type of pest and the environment. Thus, the compounds of this invention may be formulated as granules of large particle size, as powdery dusts, as wettable powders, as emulsifiable concentrates, as solutions, and the like.

Dusts and admixtures of the active ingredients with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as dispersants and carriers for the toxicant. These finely divided solids have an average particle size of less than about 50 microns. A typical dust formulation useful herein contains 10.0 parts of α-cyano-3-phenoxybenzyl 3-[β-(4-chlorophenyl)vinyl]-2,2-dimethylcyclopropanecarboxylate, 30.0 parts of bentonite clay, and 60.0 parts of talc.

The compounds of the present invention may be made into liquid concentrates by solution or emulsion in suitable liquids, and into solid concentrates by admixtures with talc, clays, and other known solid carriers used in the pesticide art. The concentrates are compositions containing about 5–50% toxicant, and 95–50% inert material which includes dispersing agents,, emulsifying agents, and wetting agents. The concentrates are diluted for practical application, with water or other liquid for sprays or with additional solid carrier for use as dusts. Typical carriers for solid concentrates (also called wettable powders) include fuller's earth, kaolin clays, silicas, and other highly absorbent, readily wet inorganic diluents. A solid concentrate formulation useful herein contains 1.5 parts each of sodium lignosulfonate and sodium laurylsulfate as wetting agents, 25.0 parts of α-cyano-3-phenoxybenzyl 3-[β-(4-chlorophenyl)vinyl]-2,2-dimethylcyclopropanecarboxylate and 72.0 parts of bentonite clay.

Useful liquid concentrates include the emulsifiable concentrates, which are homogeneous liquid or paste compositions readily dispersed in water or other dispersant, and may consist entirely of the toxicant with a liquid or solid emulsifying agent, or may also contain a liquid carrier such as xylene, heavy aromatic naphthas, isophorone and other nonvolatile organic solvents. For application, these concentrates are dispersed in water or other liquid carrier, and normally applied as a spray to the area to be treated.

Typical wetting, dispersing or emulsifying agents used in pesticidal formulations include, for example, the alkyl and alkylaryl sulfonates and sulfates and their sodium salts; alkylamide sulfonates, including fatty methyl taurides; alkylaryl polyether alcohols, sulfated higher alcohols, polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1–15% by weight of the pesticidal composition.

Other useful formulations include simple solutions of the active ingredient in a solvent in which it is completely soluble at the desired concentration, such as acetone or other organic solvents.

The concentration of the toxicant in the dilution generally used for application is normally in the range of about 2% to about 0.001%. Many variations of spraying and dusting compositions in the art may be used, by substituting a compound of this invention into compositions known or apparent to the art.

Pesticidal compositions may be formulated and applied with other active ingredients, including other insecticides, nematicides, acaricides, fungicides, plant growth regulators, fertilizers, etc. In applying the chemicals, it is obvious that an effective amount and concentration of the compound of the invention should be employed. For agricultural application the active ingredient of the invention may be applied at a rate of 75 to 4000 g per hectare, preferably 150 to 3000 g per hectare.

It is apparent that many modifications may be made in the structure, preparation, formulation and application of the compounds of this invention, without departing from the spirit and scope of the invention and of the following claims.

Table 1

| Initial Toxicity to Insects and Mites | | | | | |
|---|---|---|---|---|---|
| Compound of | Conc. | % Kill | | | |
| Example 1 | (PPM) | AW | PA | M | MWB |
| Trans (E) | 1250 | 100 | 100 | 100 | 100 |
| | 312 | 57 | 73 | 28 | 95 |

AW: Southern army worm
PA: Pea aphid
M: Two-spotted spider mite
MWB: Milkweed bug Table 2

| Insecticidal Activity Against House Flies and German Cockroaches | | | | | |
|---|---|---|---|---|---|
| | | Level I Tests | | Level II Tests | |
| Compound of | | % Knockdown | % Kill | % Knockdown | % Kill |
| Example I-D | HF | 0 | 95 | 0 | 0 |
| [Trans (E)] | GC | 0 | 60 | 0 | 0 |
| Example I-E | HF | 45 | 100 | 10 | 90 |
| (Mixed Isomers) | GC | 0 | 100 | 0 | 100 |

HF — House Flies
GC — German Cockroaches
ND — No Data

I claim:
1. An insecticidal compound of the formula:

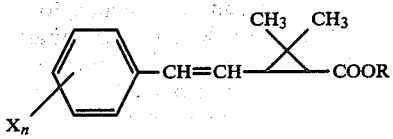

in which

X is halogen, cyano, nitro, aryl, aralkyl, aryloxy, arylthio, alkyl of $C_1-C_4$, alkoxy of $C_1-C_4$, alkylthio of $C_1-C_4$, haloalkyl of $C_1-C_2$, dialkylamino in which alkyls are $C_1-C_2$, or methylenedioxy; n is 1, 2, or 3; and R is an alcohol residue selected from the group consisting of:
(a) a benzyl- or phenoxy-substituted benzyl group of the formula:

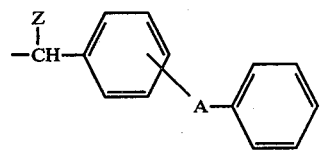

wherein Z is hydrogen, methyl, cyano, ethynyl, or phenyl, and A is —O— or —CH$_2$—;
(b) a benzyl- or phenoxy-substituted furylmethyl group;
(c) an imidomethyl group selected from the group consisting of maleimidomethyl, phthalimidomethyl, and tetrahydrophthalimidomethyl; and,
(d) a benzyl group substituted in at least two ring positions with chloro, methyl, or methylenedioxy groups.

2. The compound of claim 1 in which X is chloro, cyano, methyl, methoxy, or methylenedioxy; and n is 1 or 2.

3. The compound of claim 2 in which R is: 3-phenoxybenzyl, α-cyano-3-phenoxybenzyl, or 5-benzyl-3-furylmethyl.

4. The compound of claim 3 which is α-cyano-3-phenoxybenzyl 3-[β-(4-chlorophenyl)vinyl]-2,2-dimethylcyclopropanecarboxylate.

5. The compound of claim 4 in which the predominant isomer is cis.

6. The insecticidal compound of claim 1 in which R is an alcohol residue selected from the group consisting of:
(a) a benzyl-or phenoxy-substituted benzyl group of the formula:

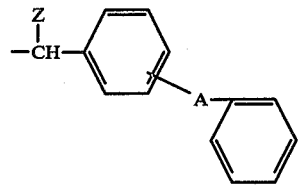

wherein Z is hydrogen, methyl, cyano, ethynyl, or phenyl and A is —O— or —CH$_2$—;
(b) 5-benzyl-3-furylmethyl;
(c) an imidomethyl group selected from the group consisting of maleimidomethyl, phthalimidomethyl, and tetrahydrophthalimidomethyl;
(d) a benzyl group substituted in at least two ring positions with chloro, methyl, or methylenedioxy groups, selected from the group consisting of 3,4-methylenedioxybenzyl, 2-chloro-4,5-methylenedioxybenzyl, and 2,4-dimethylbenzyl.

7. The compound of claim 1 in which X is selected from the group consisting of fluoro, chloro, and bromo and n is 1 or 2.

8. An insecticidal composition comprising an insecticidally effective amount of a compound of claim 1 in admixture with an agriculturally acceptable extender.

9. An insecticidal composition of claim 8 which contains a surface active agent.

10. A method of controlling insects which comprises applying to the locus where control is desired an insecticidally effective amount of a compound of claim 1.